US012377185B2

(12) United States Patent
Weindl et al.

(10) Patent No.: US 12,377,185 B2
(45) Date of Patent: *Aug. 5, 2025

(54) SEALANT DRESSING WITH PROTECTED REACTIVE COMPONENTS (71) Applicant: Ethicon, Inc., Somerville, NJ (US)

(72) Inventors: Thomas Weindl, Somerville, NJ (US); Xuejun Jay Liu, Somerville, NJ (US); Gerard Llanos, Somerville, NJ (US); Yi-Lan Allen Wang, Hillsborough, NJ (US); Wilai Kosol, Somerset, NJ (US)

(73) Assignee: Ethicon, Inc., Raritan, NJ (US)

(*) Notice: Subject to any disclaimer, the term of this patent is extended or adjusted under 35 U.S.C. 154(b) by 336 days.

This patent is subject to a terminal disclaimer.

(21) Appl. No.: 17/007,712

(22) Filed: Aug. 31, 2020

(65) Prior Publication Data

US 2022/0062492 A1 Mar. 3, 2022

(51) Int. Cl.
A61L 15/22 (2006.01)
A61L 15/18 (2006.01)
A61L 15/32 (2006.01)
A61L 15/64 (2006.01)
B32B 27/08 (2006.01)

(52) U.S. Cl.
CPC ............. A61L 15/225 (2013.01); A61L 15/18 (2013.01); A61L 15/325 (2013.01); A61L 15/64 (2013.01); B32B 27/08 (2013.01); A61L 2300/608 (2013.01); A61L 2400/16 (2013.01); B32B 2250/03 (2013.01); B32B 2250/24 (2013.01); B32B 2307/7163 (2013.01); B32B 2535/00 (2013.01)

(58) Field of Classification Search
None
See application file for complete search history.

(56) References Cited

U.S. PATENT DOCUMENTS

| | | | |
|---|---|---|---|
| 3,364,200 | A | 1/1968 | Ashton et al. |
| 3,871,376 | A | 3/1975 | Kozak |
| 4,626,253 | A | 12/1986 | Broadnax, Jr. |
| 5,002,551 | A | 3/1991 | Linsky et al. |
| 5,007,916 | A | 4/1991 | Linsky et al. |
| 5,180,398 | A | 1/1993 | Boardman et al. |

(Continued)

FOREIGN PATENT DOCUMENTS

| | | |
|---|---|---|
| CA | 3053647 A1 | 9/2018 |
| EP | 2279711 A1 | 2/2011 |

(Continued)

OTHER PUBLICATIONS

International Search Report and Written Opinion for PCT Application No. PCT/IB2021/057063, 11 pages, 2021.

(Continued)

Primary Examiner — Isis A Ghali
(74) Attorney, Agent, or Firm — David R. Crichton; Leo B. Kriksunov (57) ABSTRACT The present invention is directed to multi-layered wound dressings having a carrier layer, at least two sublayers, wherein each sublayer contains at least one reactive, cross-linkable component and the at least two reactive, cross-linkable components are co-reactive with the other and at least one reactive, cross-linkable has a protective leaving group and a buffering salt agent.

4 Claims, 3 Drawing Sheets (56) References Cited

U.S. PATENT DOCUMENTS

| | | |
|---|---|---|
| 5,484,913 A | 1/1996 | Stilwell et al. |
| 6,152,943 A | 11/2000 | Sawhney |
| 6,165,201 A | 12/2000 | Sawhney et al. |
| 6,179,862 B1 | 1/2001 | Sawhney |
| 6,443,964 B1 | 9/2002 | Ory et al. |
| 6,500,777 B1 | 12/2002 | Wiseman et al. |
| 6,514,534 B1 | 2/2003 | Sawhney |
| 6,566,406 B1 | 5/2003 | Pathak |
| 6,605,294 B2 | 8/2003 | Sawhney |
| 6,673,093 B1 | 1/2004 | Sawhney |
| 6,703,047 B2 | 3/2004 | Sawhney et al. |
| 6,818,018 B1 | 11/2004 | Sawhney |
| 7,009,034 B2 | 3/2006 | Pathak et al. |
| 7,021,086 B2 | 4/2006 | Ory et al. |
| 7,335,220 B2 | 2/2008 | Khosravi |
| 7,347,850 B2 | 3/2008 | Sawhney |
| 8,470,355 B2 | 6/2013 | Skalla et al. |
| 9,272,073 B2 | 3/2016 | Ladet et al. |
| 9,855,372 B2 | 1/2018 | Ladet |
| 9,889,230 B2 | 2/2018 | Bennett et al. |
| 10,525,170 B2 | 1/2020 | Havenstrite et al. |
| 2003/0012734 A1 | 1/2003 | Pathak et al. |
| 2003/0035786 A1 | 2/2003 | Hendriks et al. |
| 2005/0004599 A1 | 1/2005 | Mcnally-heintzelman et al. |
| 2005/0080372 A1* | 4/2005 | Nielsen ............... A61F 13/0203 602/42 |
| 2005/0113849 A1 | 5/2005 | Popadiuk |
| 2008/0071300 A1 | 3/2008 | Popadiuk et al. |
| 2008/0260802 A1 | 10/2008 | Sawhney et al. |
| 2010/0152683 A1 | 6/2010 | Lindgren et al. |
| 2010/0280546 A1 | 11/2010 | Campbell |
| 2011/0045047 A1* | 2/2011 | Bennett ............... A61L 27/34 424/422 |
| 2011/0189287 A1 | 8/2011 | Abbott et al. |
| 2011/0251574 A1 | 10/2011 | Hedrich et al. |
| 2014/0249575 A1* | 9/2014 | Mylonakis ............... A61L 24/02 606/214 |
| 2017/0319193 A1 | 11/2017 | Pulapura et al. |
| 2018/0028166 A1 | 2/2018 | Mylonakis |
| 2022/0023488 A1* | 1/2022 | Nativ ............... A61L 15/425 |

FOREIGN PATENT DOCUMENTS

| | | |
|---|---|---|
| GB | 2485637 A | 5/2012 |
| WO | 2007117237 A1 | 10/2007 |
| WO | 2010002435 A2 | 1/2010 |
| WO | WO 2010059280 A2 | 5/2010 |
| WO | WO 2018165409 A1 | 9/2017 |
| WO | 2022018611 A1 | 1/2022 |
| WO | 2022043796 A1 | 3/2022 |

OTHER PUBLICATIONS

International Search Report and Written Opinion Received for PCT Application No. PCT/IB2021/056501, mailed on Oct. 8, 2021, 11 Pages.

Xiaowei, He, "Functional Material of Carbohydrate", China Light Industry Press, pp. 328, Jan. 2007.

Zhengnong, Xia, "(Dacihai: Chemical Industry Light Industry Textile Volume", Shanghai Lexicographical Publishing House, p. 222, Aug. 2009.

* cited by examiner

*Figure 5:* Plot of Maximum Load (N) vs weight sample groups (Left) and Tukey's test results (Right)

*Figure 6:* Plot of Maximum load(N) vs surface morphology sample groups (Left) and Tukey's test results (Right)

SEALANT DRESSING WITH PROTECTED REACTIVE COMPONENTS

BACKGROUND

Absorbable hemostatic patches containing two cross-linkable components have been described in the literature including in US Publication No. 2011/0045047 A1. The cross-linkable components for such patches can be a pair of co-reactive compounds or a carrier substrate coated with a co-reactive compound having available units that can form covalent cross-links with the corresponding co-reactive group on the carrier substrate. The major constraints for such patents is that the co-reactive components can react in an aqueous/moist environment which may reduce the patch potency over time. One practice for overcoming this problem has been to process and package the co-reactive containing patches under low moisture conditions. Another practice has been to create some space or separation between the co-reactive layers by applying coatings on opposite sides of a dressing or by placing a film barrier layer between the co-reactive components.

Applicants have identified an alternative method to improve stability and efficacy wherein one or more of the co-reactive, cross-linkable components applied onto the dressing are chemically modified with a protective leaving group and delivered with a buffering salt agent.

SUMMARY OF THE INVENTION

The present invention is directed to multi-layered wound dressings having a carrier layer, at least two sublayers, wherein each sublayer contains at least one reactive, cross-linkable component and the at least two reactive, cross-linkable components are co-reactive with the other and at least one reactive, cross-linkable has a protective leaving group and a buffering salt agent. The wound dressing can have at least two separate co-reactive-containing sublayers. The carrier layer can have at least two chemical distinct layers that are structurally integrated via ultrasonic welding, needle punching, heat welding, chemical attachment, suture attachment or combinations thereof.

The at least one protected reactive cross-linkable component can have substantially all amine groups end-capped with a hydrohalide leaving group. In one embodiment, the at least one protected reactive group is a PEG-amine with protective leaving groups on substantially all primary amine groups. The protective leaving group can react with the buffer to render the primary amine groups available for reaction.

The two separate co-reactive-containing sublayers can be provided in the form of first layer having a component that is co-reactive with groups available within a second, preferably opposing sublayer that is a co-reactive crosslinkable protected group.

The carrier and the two sublayers can be arranged in a stacked alignment. In one embodiment, the carrier has three stacked sublayer coatings with a buffering agent, a co-reactive crosslinkable agent and a protected co-reactive crosslinkable agent. The buffering agent sublayer can be immediately adjacent to the carrier layer, the protected co-reactive crosslinkable coated sublayer agent is adjacent to the buffering agent coated sublayer and the co-reactive crosslinkable agent coated sublayer is a top layer immediately adjacent to the protected co-reactive crosslinkable coated sublayer. In another embodiment, the multi-layered wound dressing can have a carrier layer with two discrete sublayers in a stacked alignment and a buffer coated sublayer adjacent to the carrier layer and a reactant coated sublayer of a protected PEG-Amine and PEG-NHS that have been co-deposited as a top layer adjacent to the buffer coated sublayer.

The buffering agent can be an alkaline compound, while the co-reactive crosslinkable agent can be PEG-NHS and the protective co-reactive crosslinkable component is a PEG-amine with a plurality of hydrohalide protective leaving groups. The buffering agent can preferably be an alkaline compound. In one embodiment, the buffering agent can be sodium borate, sodium tetraborate, or disodium tetraborate, 2-(N-morpholino) ethanesulfonic acid (MES), tris(hydroxymethyl)aminomethane (TRIS), Bis-tris methane (Bis-Tris), sodium carbonate, sodium bicarbonate, sodium acetate, and combinations thereof.

In one embodiment, the multi-layered wound dressings as described above have been subjected to pliabilization to increase flexibility. In another embodiment, the wound dressings described above have been subjected to roller compression pliabilization.

The present invention also relates to methods of manufacturing the multi-layered wound dressings described above by spray coating a coating substrate with layers of a co-reactive crosslinkable agents and a buffering agent. The present invention also relates to methods of treatment that comprise applying the multi-layered wound dressings described above on tissue.

DETAILED DESCRIPTION

The dressing of the present invention includes a carrier layer having at least two sublayers that contain co-reactive, cross-linkable components and a buffering agent layer. The carrier layer can have at least two chemically distinct layers that are structurally integrated via ultrasonic welding, needle punching, heat welding, chemical attachment, suture attachment. In a still further alternative embodiment, the wound dressing can be provided with at least two discrete co-reactive-containing layers and combined with or delivered in conjunction with a buffering salt agent, preferably as an alkaline buffer.

The carrier substrate and substrate layers can optionally be in the form of woven, non-woven or porous sponge materials. Exemplary materials of construction are cellulosic, synthetic polymers, gelatin, collagen and extra cellular matrix. The carrier substrate and sublayers may be comprised of components selected from gelatin, collagen, oxidized polysaccharides, aliphatic polyester polymers and/or copolymers of one or more monomers selected from the group consisting of D-lactic acid, L-lactic acid, lactide (including L-, D-, meso forms), glycolic acid, glycolide, caprolactone, p-dioxanone and trimethylene carbonate and mixtures or blends thereof. Biodegradable polyurethanes prepared using, but not limited to, diisocyanates such as Ethyl 2,6-diisocyanatohexanoate (ELDI) and Methyl 2,6-diisocyanatohexanoate (MLDI) together with degradable aliphatic polyester diols and with degradable chain extenders such as 2-Hydroxyethyl-2-hydroxypropanoate, 4-((1-(1-Amino-2-phenylethoxy) ethoxy)methylcyclohexyl)methyl-2-amino-3-phenylpropanoate, 1,1-(Hexane-1,6-diyl)bis(3-(2-hydroxyethylurea, Ethane-1,2-diyl bis(3-(4-hydroxyphenyl)propanoate, Bis(2-hydroxyethyl)phosphate and Bis(2-hydroxyhexyl)phosphate may also be suitable for preparing the substrates.

In one form, the carrier substrate is comprised of layers of oxidized polysaccharides, in particular oxidized cellulose and the neutralized derivatives thereof. For example, the cellulose may be carboxylic-oxidized or aldehyde-oxidized cellulose. In one form, oxidized regenerated polysaccharides including, but without limitation, oxidized regenerated cellulose may be used to prepare the second absorbable woven or knitted fabric. Regenerated cellulose possesses a higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of which are hereby incorporated by reference as if set forth in its entirety. Examples of fabrics that may be utilized include, but are not limited to, Interceed absorbable adhesion barrier, Surgicel absorbable hemostat; Surgicel Nu-Knit absorbable hemostat; and Surgicel Fibrillar absorbable hemostat; each available from Ethicon, Inc., Somerville, N.J. U.S. Pat. No. 5,007,916 discloses the aforementioned Interceed absorbable adhesion barrier and methods for making same, the contents of which are hereby incorporated by reference for all that they disclose.

The carrier substrate can alternatively, or additionally, be comprised of layers of fabric of aliphatic polyester polymers, copolymers, or blends thereof. The aliphatic polyesters are typically synthesized in a ring opening polymerization of monomers including, but not limited to, lactide (including L-, and D-, meso forms), glycolic acid, glycolide, caprolactone, p-dioxanone (1,4-dioxan-2-one), and trimethylene carbonate (1,3-dioxan-2-one). The aliphatic polyesters, in some cases, can be made by polycondensation of for instance, D-lactic acid, L-lactic acid and/or glycolic acid. In one form, the fabric comprises a copolymer of glycolide and lactide, in an amount ranging from about 70 to 95% by molar basis of glycolide and the remainder lactide.

The carrier substrate may also comprise an oxidized regenerated cellulose/polypropylene/polydioxanone (PDS) mesh, commercially available from Ethicon, Inc. under the tradename, Proceed. U.S. Patent Publication Nos. 2005/0113849A1 and 2008/0071300A1 disclose the aforementioned Proceed oxidized regenerated cellulose/polypropylene/PDS mesh substrate and methods for making same, the contents of which are hereby incorporated by reference for all that they disclose. In one form, both exterior surfaces of the oxidized regenerated cellulose/polypropylene/PDS mesh may be substantially coated with the polymeric coating, and in another form only one exterior surface of this substrate may be substantially coated with the polymeric coating. The fabric used to form the substrate may be comprised of aliphatic polyester polymers, copolymers, or blends thereof alone or in combination with oxidized polysaccharide fibers.

In one embodiment, the carrier substrate is made from layers of biomaterials selected from the group consisting of a biomaterial, preferably a protein, a biopolymer or a polysaccharide matrix, especially a collagen, gelatin, fibrin, starch or chitosan matrix, and mixtures thereof. Preferably, the matrix of the present invention is biodegradable, i.e. it is naturally absorbed by the patient's body after some time. In any way, the material (including the matrix) must be biocompatible, i.e. have no harming effect to the patient to whom the material is administered. Such biodegradable materials are specifically suitable in situations where hemostasis is achieved inside the body, i.e. in the course of surgery and the site is closed after surgery.

Accordingly, in one embodiment, the carrier substrate is preferably a biomaterial selected from biopolymers such as a protein, or a polysaccharide. Especially preferred is a biomaterial selected from the group consisting of collagen, gelatin, fibrin, a polysaccharide, e.g. hyaluronic acids, chitosan, and a derivative thereof, more preferred gelatin, collagen and chitosan, especially preferred gelatin and collagen. Such gelatin or collagen matrix used for the present invention can be derived from any collagen suitable to form a gel, including a material from liquid, pasty, fibrous or powdery collagenous materials that can be processed to a porous or fibrous matrix as well as particles. The preparation of a collagen gel for the production of a sponge or sheet may include acidification until gel formation occurs and subsequent pH neutralization. To improve gel forming capabilities or solubility the collagen may be (partially) hydrolyzed or modified, as long as the property to form a stable sponge or sheet when dried is not diminished. The matrix used for coupling the thrombin receptor activating agent can be a biopolymer, i.e., a naturally occurring polymer or a derivative thereof, or can be a synthetic polymer. Examples of biopolymers useful in a hemostatic material according to the present invention include polypeptides such as collagen, collagen derivatives such as gelatin, elastin, and elastin derivatives.

Collagen-containing embodiments in accordance with the present disclosure include a porous carrier substrate having a first co-reactive and cross-linkable component applied to a first portion of the porous carrier substrate and a second co-reactive and cross-linkable component applied to a second portion of the porous carrier substrate.

The porous carrier substrate of the dressing has openings or pores over at least a portion of a surface thereof. As described in more detail below, suitable materials for forming the porous carrier substrate include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous carrier substrate. Woven fabrics, knitted fabrics and open cell foam are illustrative examples of structures in which the pores can be in sufficient number and size so as to interconnect across the entire thickness of the porous carrier substrate. In embodiments, the pores do not interconnect across the entire thickness of the porous carrier substrate. Closed cell foam or fused non-woven materials are illustrative examples of structures in which the pores may not interconnect across the entire thickness of the porous carrier substrate. The pores of the foam porous substrate may span across the entire thickness of porous carrier substrate. In yet other embodiments, the pores do not extend across the entire thickness of the porous carrier substrate, but rather are present at a portion of the thickness thereof. In embodiments, the openings or pores are located on a portion of the surface of the porous carrier substrate, with other portions of the porous carrier substrate having a non-porous texture.

Where the porous carrier substrate is fibrous, the porous carrier substrate may be formed using any method suitable to forming fibrous structures, including but not limited to knitting, weaving, non-woven techniques, wet-spinning, electro-spinning, extrusion, co-extrusion, and the like. Suitable techniques for making fibrous structures are within the purview of those skilled in the art. In embodiments, the textile has a three dimensional structure, such as the textiles described in U.S. Pat. Nos. 7,021,086 and 6,443,964, the disclosures of which are incorporated herein by this reference in their entirety.

In embodiments, the porous carrier substrate is made from fibers of oxidized cellulose. Such materials are known and include oxidized cellulose hemostat materials commercially available under the trade name SURGICEL. Methods for preparing oxidized cellulose hemostat materials are known to those skilled in the art and are disclosed, for example in U.S. Pat. Nos. 3,364,200; 4,626,253; 5,484,913; and 6,500,777, the disclosures of which are incorporated herein by this reference in their entirety.

Where the porous carrier substrate is a foam, the porous carrier substrate may be formed using any method suitable to forming a foam or sponge including, but not limited to the lyophilization or freeze-drying of a composition. The foam may be cross-linked or non-cross-linked, and may include covalent or ionic bonds. Suitable techniques for making foams are within the purview of those skilled in the art.

One or more sublayers of the porous carrier substrate can be at least 0.1 cm thick, in certain embodiments from about 0.2 to about 1.5 cm thick. The size of the pores in the sublayers of the porous carrier substrate can be from about 2 micrometers to about 300 micrometers, in embodiments from about 50 micrometers to about 150 micrometers. It is envisioned that the pores of the sublayers of the substrate may be arranged in any manner in the substrate. For example, the pores may be configured in a random or uniform manner. In some embodiments, the pores may be formed with the use of copper alginate to create a honeycomb shaped porous substrate. In still other embodiments, the pores may be configured to create a gradient in the porous substrate. The gradient may further enhance the porous substrates ability to absorb the physiologic fluid and direct the migration of the physiological fluid carrying the first co-reactive component towards the second co-reactive component.

In embodiments, the dressing is a made from non-denatured collagen or collagen which has at least partially lost its helical structure through heating or any other method, consisting mainly of non-hydrolyzed alpha. chains, of molecular weight close to 100 kDa. The term "non-denatured collagen" means collagen which has not lost its helical structure. The collagen used for the dressing of present dressing may be native collagen or atelocollagen, notably as obtained through pepsin digestion and/or after moderate heating as defined previously. The collagen may have been previously chemically modified by oxidation, methylation, ethylation, succinylation or any other known process. The collagen may also be cross-linked with any suitable cross-linker, such as genipin, isocyanates, and aldehydes. The origin and type of collagen may be as indicated for the non-dressing described above.

In other embodiments, gelatin or collagen, including any collagen described herein, may be utilized as one of the precursors. As described in greater detail below, amine groups on a collagen precursor, which are nucleophilic, may be free to react with electrophilic groups on a first co-reactive component, thereby forming a substrate of the present disclosure.

In embodiments, the carrier substrate or a porous collagen layer thereof can be obtained by freeze-drying an aqueous acid solution of collagen at a concentration of 2 to 50 grams/liter (g/l) and an initial temperature of 4 to 25 C. The concentration of collagen in the solution can be from about 1 g/l to about 30 g/l, in embodiments about 10 g/l. This solution is advantageously neutralized to a pH of around 6 to 8. The dressing can also be obtained by freeze-drying a fluid foam prepared from a solution of collagen or heated collagen, emulsified in the presence of a volume of air in variable respective quantities (volume of air:water varying from about 1 to about 10).

In one embodiment, the carrier substrate has a first co-reactive component applied onto a first sublayer and a second co-reactive component applied thereto. The terms "first co-reactive component" and "second co-reactive component" each means a polymer, functional polymer, macromolecule, small molecule, or cross-linker that can take part in a reaction to form a network of cross-linked molecules, such as, a hydrogel.

In one embodiment, each of the first and second co-reactive components is multifunctional, meaning that it comprises two or more electrophilic or nucleophilic functional groups, such that, for example, a nucleophilic functional group on the first co-reactive component may react with an electrophilic functional group on the second co-reactive component to form a covalent bond. At least one of the first or second co-reactive components includes more than two functional groups, so that, as a result of electrophilic-nucleophilic reactions, the precursors combine to form cross-linked polymeric products. Such reactions are referred to as "cross-linking reactions".

In certain embodiments, each of the first and second co-reactive components includes only one category of functional groups, either only nucleophilic groups or only electrophilic functional groups, so long as both nucleophilic and electrophilic precursors are used in the cross-linking reaction. Thus, for example, if the first co-reactive component has nucleophilic functional groups such as amines, the second co-reactive component may have electrophilic functional groups such as N-hydroxysuccinimides. On the other hand, if first co-reactive component has electrophilic functional groups such as sulfosuccinimides, then the second co-reactive component may have nucleophilic functional groups such as amines or thiols. Thus, functional polymers such as proteins, poly(allyl amine), styrene sulfonic acid, or amine-terminated di- or multifunctional poly(ethylene glycol) ("PEG") can be used.

The first and second co-reactive components may have biologically inert and water soluble cores. When the core is a polymeric region that is water soluble, preferred polymers that may be used include: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly(amino acids); poly(saccharides), such as dextran, chitosan, alginates, carboxymethylcellulose, oxidized cellulose, hydroxyethylcellulose, hydroxymethylcellulose, hyaluronic acid; and proteins such as albumin, collagen, casein, and gelatin. The polyethers and more particularly poly(oxyalkylenes) or poly(ethylene glycol) or polyethylene glycol are especially useful. When the core is small molecular in nature, any of a variety of hydrophilic functionalities can be used to make the first and second co-reactive components water soluble. For example, functional groups like hydroxyl, amine, sulfonate and carboxylate, which are water soluble, maybe used to make the precursor water soluble. In addition, N-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

In certain embodiments, both the first and second co-reactive components may be large molecules that are capable of cross-linking. For example, in embodiments, one of the precursors may be a multi-functional PEG having a molecular weight of from about 2,000 to about 20,000 Daltons. This multi-functional PEG, in embodiments possessing electrophilic groups, may be reacted with a collagen having a molecular weight of about 100,000 Daltons. In other embodiments, a gelatin having a molecular weight of from about 50,000 to about 100,000 Daltons may be used in place of the collagen.

In all embodiments, at least one of the co-reactive components has a protective leaving group and a buffering salt agent is provided as a sublayer. The PEG-amine can, for example, be provided in a salt-form, such as a chloride salt form of a PEG-amine, as the protective leaving group. Examples of the preferred buffering salt agents are disodium tetraborate (Borax), 2-(N-morpholino)ethanesulfonic acid (MES), tris(hydroxymethyl)aminomethane (TRIS), Bis-tris methane (Bis-Tris), sodium carbonate or bicarbonate, sodium acetate, and combinations thereof.

In an alternative embodiment, the co-reactive components and buffering agent are provided on a patch. An exemplary sealing patch/pad comprises: PEG-NH2*HCl and PEG-NHS, a buffering salt agent, preferably as an alkaline buffer, each deposited as layers on an absorbable substrate.

If it is desired that the biocompatible cross-linked polymer resulting from the reaction of the first and second co-reactive components be biodegradable or absorbable, one or more of the first and second co-reactive components may have biodegradable linkages present between the functional groups. The biodegradable linkage optionally also may serve as the water soluble core of one or more of the precursors. In the alternative, or in addition, the functional groups of the first and second co-reactive components may be chosen such that the product of the reaction between them results in a biodegradable linkage. For each approach, biodegradable linkages may be chosen such that the resulting biodegradable biocompatible cross-linked polymer will degrade, dissolve or be absorbed in a desired period of time. Preferably, biodegradable linkages are selected that degrade under physiological conditions into non-toxic products.

The biodegradable linkage may be chelates or chemically or enzymatically hydrolyzable or absorbable. Illustrative chemically hydrolyzable biodegradable linkages include polymers, copolymers and oligomers of glycolide, d-lactide, lactide, caprolactone, dioxanone, and trimethylene carbonate. Illustrative enzymatically hydrolyzable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(amino acid)s, poly(carbonate)s, poly(saccharide)s and poly(phosphonate)s. In embodiments, the biodegradable linkage may contain ester linkages. Some non-limiting examples include esters of succinic acid, glutaric acid, propionic acid, adipic acid, or amino acids, as well as carboxymethyl esters.

In embodiments, a multifunctional electrophilic polymer such as a multi-arm PEG functionalized with multiple NHS groups may be used as a first co-reactive component, and a multifunctional nucleophilic component such as trilysine may be used as a second co-reactive component. In other embodiments, a multifunctional electrophilic polymer such as a multi-aim PEG functionalized with multiple NHS groups may be used as a first co-reactive component, and a multifunctional nucleophilic polymer such as collagen and/or a collagen derivative may be used as a second co-reactive component. The multi-arm PEG functionalized with multiple NHS groups can for example have four, six or eight arms and have a molecular weight of from about 5,000 to about 25,000. Many other examples of suitable first and second precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire content of each of which is incorporated herein by reference.

For the patch embodiment, the co-reactive components and buffering agent can be deposited upon the matrix as individual layers. Alternatively, the co-reactive components can be deposited as a mixture while the buffering agent is provided as a separate layer. The ordering of layers may change, but the preferred order for coating the patch or pad with PEG-NH2*HCl (or any other hydrohalide), PEG-NHS, and a buffering salt (such as disodium tetraborate, MES, TRIS, Bis-Tris, sodium bicarbonate), begins with the matrix, then a layer of buffering salt, a layer of protected PEG-amine and a layer of the PEG-NHS.

Furthermore, the number of arms and molecular weight of materials may change, but 4-arm-10K-NH2*HCl and 4-arm-10K-NHS are preferred variants from an efficacy and stability standpoint. The embodiment was evaluated with different order of coating. Performance and stability is greatly impacted by the location of the deposited buffer on the matrix using the spray-coating process. When buffer was deposited below both PEGs (i.e., furthest away from the tissue when matrix is applied), the performance and stability were optimal.

The first co-reactive component may be applied to the porous carrier substrate using any suitable method known to those skilled in the art, including, but not limited to spraying, brushing, dipping, pouring, laminating, etc. In embodiments, the first co-reactive component may be applied as a coating on the carrier substrate in any concentration, dimension and configuration capable of forming a hemostatic dressing. In embodiments, the first co-reactive component coating may penetrate the pores of the porous carrier substrate. In embodiments, the first co-reactive component may be applied to the porous substrate as a film that is laminated onto at least one side of the substrate.

The patch embodiment was evaluated with and without the presence of a deposited buffer on the matrix. When 0.2 M TRIS (pH=7.4) was used as a medium during Tissue Peel testing, the buffering capacity was not sufficient to de-protect the PEG-NH2*HCl, resulting in poor adhesion to the tissue. When the medium was exchanged for 1M sodium bicarbonate (pH=8.3), PEG-NH2*HCl was sufficiently de-protected, enabling improved adhesive properties over the standard formulation as a control. In providing the buffer on the matrix itself, as described in Embodiments 1 and 2, the need for sufficient pre-existing buffering capacity in blood or bodily fluid is eliminated as the buffer is provided within the product.

The second co-reactive component and buffering agent likewise may be applied to the porous substrate using any suitable method known to those skilled in the art, including, but not limited to spraying, brushing, dipping, pouring, laminating, etc. In still other embodiments, the second co-reactive component and buffering agent may each be applied to the porous substrate in solution followed by evaporation or lyophilization of the solvent. In embodiments, the second co-reactive component and buffering may each be applied to the porous substrate as a coating on at least one side of the carrier substrate or as a film laminated onto at least one side of the carrier substrate.

It should be understood that, as an alternative to foamed collagen or gelatin, the porous carrier substrate may be a fibrous structure. Thus, in embodiments, the porous substrate may be a fibrous structure, i.e., a woven or non-woven structure. The first and second co-reactive components and buffering agent can be applied to a fibrous porous carrier substrate using substantially the same techniques described above with respect to foam porous carrier substrate. Accordingly, as with the foam porous carrier substrates described above, where the porous carrier substrate is fibrous, the first and/or second co-reactive components and buffering agent may be applied, for example as particles deposited from a solution, non-porous films formed by drying a film-forming solution, or as a foam applied to at least a portion of the fibrous porous carrier substrate.

In one embodiment, one or more sublayers comprises a nonwoven fabric and a reinforcement fabric. The reinforcement fabric provides a backing to which the nonwoven fabric may be attached, either directly or indirectly. The nonwoven fabric functions as the first absorbable nonwoven fabric of the reinforced absorbable multilayered fabric described herein. The first absorbable nonwoven fabric is comprised of fibers comprising aliphatic polyester polymers, copolymers, or blends thereof. The aliphatic polyesters are typically synthesized in a ring opening polymerization of monomers including, but not limited to, lactic acid, lactide (including L-, D-, meso and D, L mixtures), glycolic acid, glycolide, .epsilon.-caprolactone, p-dioxanone (1,4-dioxan-2-one), and trimethylene carbonate (1,3-dioxan-2-one). Preferably, the first absorbable nonwoven fabric comprises a copolymer of glycolide and lactide, in an amount ranging from about 70 to 95% by molar basis of glycolide and the remainder lactide.

In an alternative embodiment, the first absorbable nonwoven fabric comprises fibers comprised of aliphatic polyester polymers, copolymers, or blends thereof, in combination with oxidized polysaccharide fibers. Preferably, the nonwoven fabric is made by processes other than spinning, weaving or knitting. For example, the nonwoven fabric may be prepared from yarn, scrims, netting or filaments that have been made by processes that include spinning, weaving or knitting. The yarn, scrims, netting and/or filaments are crimped to enhance entanglement with each other and attachment to the second absorbable woven or knitted fabric. Such crimped yarn, scrims, netting and/or filaments may then be cut into staple that is long enough to entangle. The staple may be between about 0.1 and 3.0 inches long, preferably between about 0.75 and 2.5 inches, and most preferably between about 1.5 and 2.0 inches. The staple may be carded to create a nonwoven batt, which may be then needlepunched or calendared into the first absorbable nonwoven fabric. Additionally, the staple may be kinked or piled.

The sublayer thickness of the nonwoven fabric may range from about 0.25 to 2 mm. The basis weight of the nonwoven fabric ranges from about 0.01 to 0.2 $g/in^2$; preferably from about 0.03 to 0.1 $g/in^2$; and most preferably from about 0.04 to 0.08 $g/in^2$. The weight percent of first absorbable nonwoven fabric may range from about 10 to 80 percent, based upon the total weight of the reinforced absorbable multilayered fabric.

The second absorbable woven or knitted fabric functions as the reinforcement fabric and comprises oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used to prepare the second absorbable woven or knitted fabric. Regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents each of which is hereby incorporated by reference as if set forth in its entirety.

The reinforcement fabric utilized in the present invention may be woven or knitted, provided that the fabric possesses the physical properties necessary for use in contemplated applications. Such fabrics, for example, are described in U.S. Pat. Nos. 4,626,253, 5,002,551 and 5,007,916, the contents of which are hereby incorporated by reference herein as if set forth in its entirety. In preferred embodiments, the reinforcement fabric is a warp knitted tricot fabric constructed of bright rayon yarn that is subsequently oxidized to include carboxyl or aldehyde moieties in amounts effective to provide the fabrics with biodegradability.

In an alternative embodiment, the second absorbable woven or knitted fabric comprises oxidized polysaccharide fibers in combination with fibers comprised of aliphatic polyester polymers, copolymers, or blends thereof.

The second absorbable woven or knitted fabric preferably comprises oxidized regenerated cellulose and may have a basis weight ranging from about 0.001 to 0.2 $g/in^2$, preferably in the range of about 0.01 to 0.1 $g/in^2$, and most preferably in the range of about 0.04 to 0.07 $g/in^2$.

The first absorbable nonwoven fabric is attached to the second absorbable woven or knitted fabric, either directly or indirectly. For example, the nonwoven fabric may be incorporated into the second absorbable woven or knitted fabric via needlepunching, calendaring, embossing or hydroentanglement, or chemical or thermal bonding. The staple of the first absorbable nonwoven fabric may be entangled with each other and imbedded in the second absorbable woven or knitted fabric. More particularly, for methods other than chemical or thermal bonding, the first absorbable nonwoven fabric may be attached to the second absorbable woven or knitted fabric such that at least about 1% of the staple of the first absorbable nonwoven fabric are exposed on the other side of the second absorbable woven or knitted fabric, preferably about 10-20% and preferably no greater than about 50%. This ensures that the first absorbable nonwoven fabric and the second absorbable woven or knitted fabric remain joined and do not delaminate under normal handling conditions. The reinforced absorbable multilayered fabric is uniform such that substantially none of the second absorbable woven or knitted fabric is visibly devoid of coverage by the first absorbable nonwoven fabric.

During use, the patch dressing is oriented with the co-reactive components applied directly onto the tissue. In certain embodiments, the first and second co-reactive portions may be distinguishable from one another by the addition of contrast dyes, surface texturing, coloring or other visual cues. Upon contact with tissue, such as, for example, injured tissue, the dressing will soak up physiological fluid and the first hydrogel will be dissolved by the fluid. As the fluid wicks into and migrates through the dressing, it will carry the dissolved first co-reactive component into the second co-reactive component and buffering agent. Eventually, the first and second co-reactive components will react to form a biocompatible cross linked material, thereby assisting tissue ingrowth and remodeling as the scaffold degrades. In some embodiments, the biocompatible cross linked material produced by reaction of the first and second co-reactive components also provide the dressing with anti-adhesive properties.

The following examples are provided for illustrative purposes only and is not intended to limit the scope of the present disclosure.

Example 1

Four example deposition patterns. Coating order is defined as proximity of a layer to the carrier substrate (1st layer is closest to the carrier substrate, 2nd layer is second closest, etc.) and represents the sequence in which the materials were deposited in the spraying process.

Figure 1:
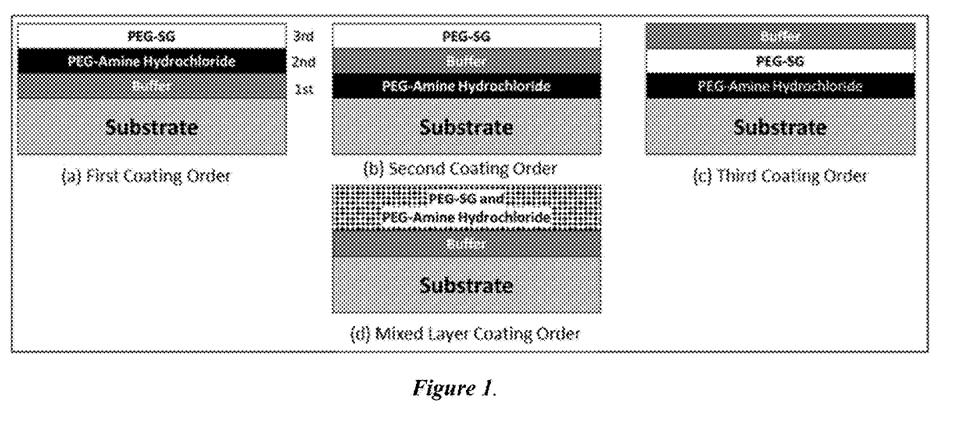
FIG. 1 illustrates embodiments of the inventive wound dressing.

Examples (a—First Coating Order), (b—Second Coating Order), and (c—Third Coating Order), as shown in FIG. 1, demonstrate unique deposited layers of a buffering salt, a protected form of PEG-Amine, and a PEG-NHS. Example (d) illustrates a mixture of a protected form of PEG-Amine and PEG-NHS co-deposited in a single homogenous layer together. The layers were applied using ultrasonic spraying for each of components onto a bi-layer carrier substrate comprising a layer of oxidized cellulose joined to a layer of fibers composed of a copolymer made from 90% glycolide and 10% L-lactide. The 4ARM-10K-PEG-Amine Hydrochloride was deposited with an average coating density of 14.2 mg/cm$^2$; the 4ARM-10K-PEG-SG was deposited with an average coating density of 17.7 mg/cm$^2$; and disodium tetraborate was used as the buffer in this study, with an average coated density of 1.0 mg/cm$^2$.

Example 2: Testing of Tissue Peel Force of Various Buffer Coating Permutations

Figure 2:
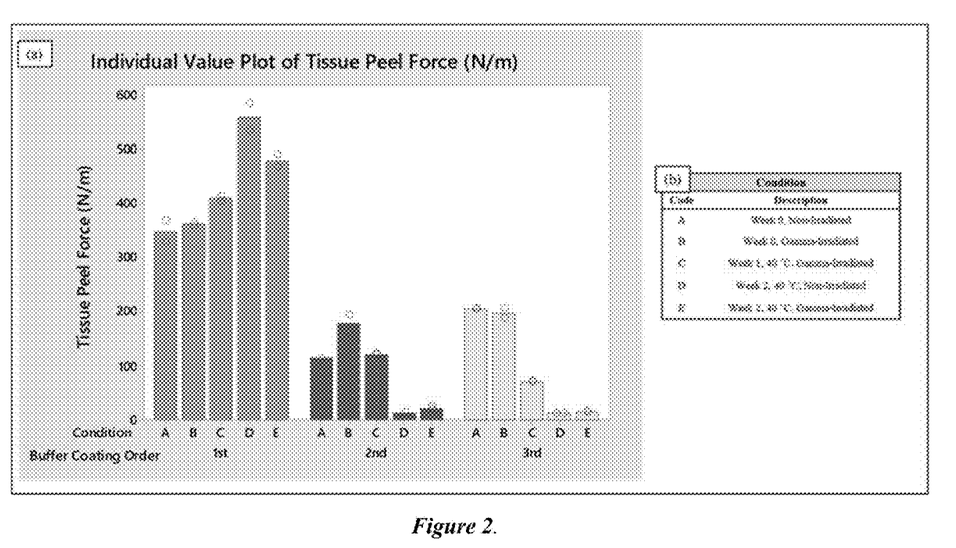
FIG. 2 illustrates a graph of tissue peel force for multiple samples.

Tissue peel force of prototypes was evaluated across an increasing severity of conditions and illustrated in FIG. 2. The least severe condition was at week 0 with no gamma-irradiation, while the most sever condition was 2 weeks of condition at 40° C. after gamma-irradiation.

Example 3: See FIG. 3

Figure 3:
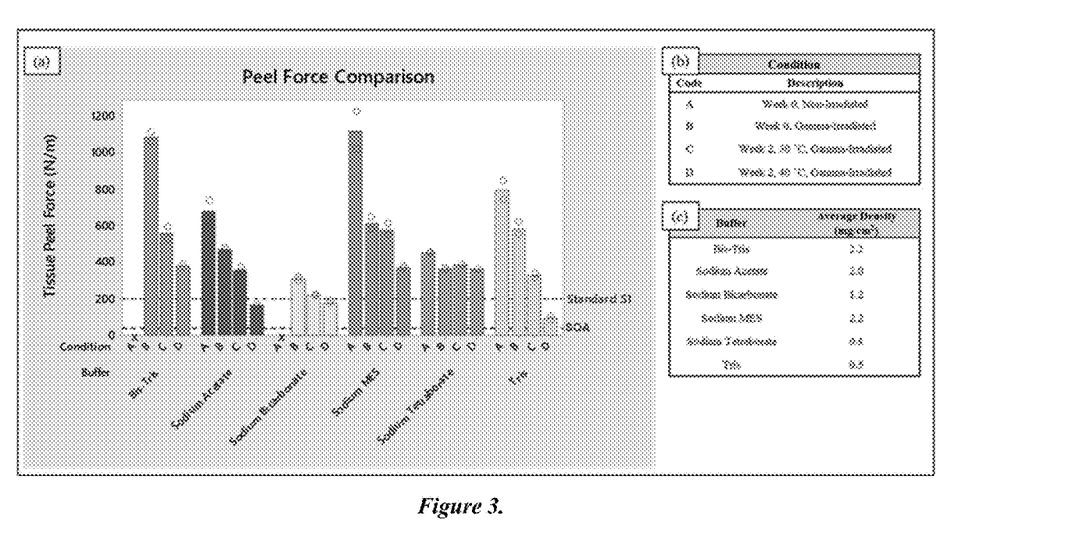
FIG. 3 illustrates a graph of comparative peel force values.

The tissue peel force (a) of a variety of prototypes with different candidate buffers—all buffers in 1st Coating Order of Example 1. Tissue peel force of prototypes was evaluated across an increasing severity of conditions (b). The least severe condition was at week 0 with no gamma-irradiation, while the most sever condition was 2 weeks of condition at 40° C. after gamma-irradiation. Target buffer densities were approximated via titration of PEG-Amine Hydrochloride with the respective buffer prior to prototype fabrication. Using ultrasonic spraying, components were deposited onto a bi-layer carrier substrate comprising a layer of oxidized cellulose joined to a layer of fibers composed of a copolymer made from 90% glycolide and 10% L-lactide. Respective buffers (e.g., Bis-Tris, sodium acetate, etc.) were deposited first onto a carrier substrate first at average coating densities of 2.2 mg/cm$^2$ for Bis-Tris, 2.0 mg/cm$^2$ for Sodium Acetate, 1.2 mg/cm$^2$ for Sodium Bicarbonate, 2.2 mg/cm$^2$ for Sodium MES, 0.8 mg/cm$^2$ for disodium tetraborate, and 0.5 mg/cm$^2$ for Tris. 4ARM-10K-PEG-Amine Hydrochloride (at 12 mg/cm$^2$) and 4ARM-10K-PEG-SG (at 18 mg/cm$^2$) were coated respectively onto the carrier substrate in sequential order after the designated buffer. Non-irradiated data from week 0 was not available for Bis-Tris and Sodium Bicarbonate prototypes. Standard S1 reference line at 200 N/m corresponds to a typical result for the tissue peel force measurement, while the 'SOA' reference line at 40 N/m corresponds to the tissue peel force for a commercially topical hemostat product comprised of an absorbable backing made of oxidized cellulose and a pair of self-adhesive hydrogel components that are not chemically protected. S1 patch corresponds to the standard formulation in which the co-reactive crosslinkable components are not protected and not provided with a buffering agent.

Example 4

Figure 4:
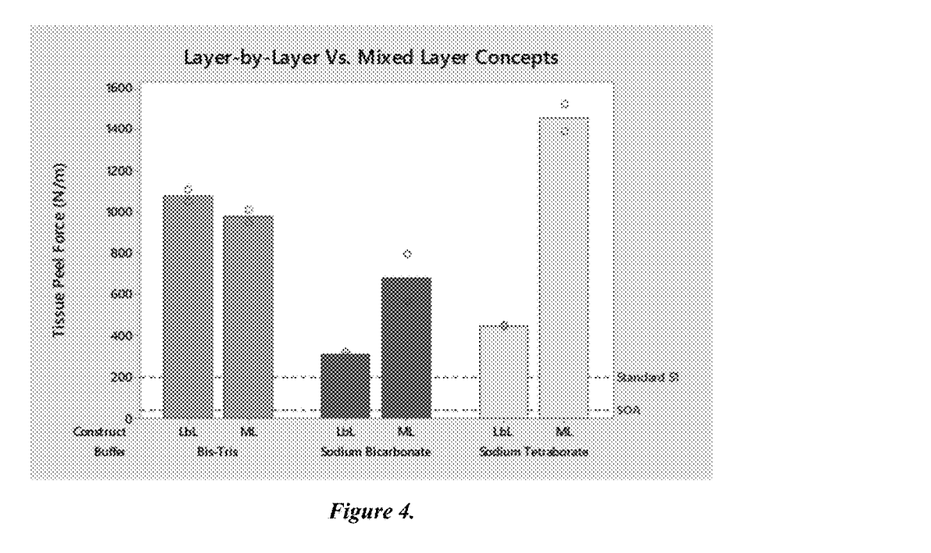
FIG. 4 illustrates comparative values for tissue peel force for various buffer agents.

Tissue Peel results for Layer-by-Layer (LbL) and Mixed Layer (ML) prototypes with different buffering materials are shown in FIG. 4. All prototypes were fabricated with a buffering agent in the First Coating Order. All results are from t=0. Using ultrasonic spraying, components were deposited onto a bi-layer carrier substrate comprising a layer of oxidized cellulose joined to a layer of fibers composed of a copolymer made from 90% glycolide and 10% L-lactide. Buffers were deposited first onto their respective carrier substrates at target coating densities of 1.9 mg/cm$^2$ for Bis-Tris, 2.4 mg/cm$^2$ for sodium bicarbonate, and 1.1 mg/cm$^2$ for disodium tetraborate. A co-mixture of 4ARM-10K-PEG-Amine Hydrochloride (at 7 mg/cm$^2$) and 4ARM-10K-PEG-SG (at 7.8 mg/cm$^2$) was coated onto the carrier substrate as a layer after the designated buffer.

When a matrix material, such as a matrix fabricated from oxidized regenerated cellulose (ORC) and polyglactin 90:10 (PG910), is coated with 4-arm-5K PEG-NH2 and 4-arm-10K PEG-NHS or 4-arm-10K PEG-NH2*HCl and 4-arm-10K PEG-NHS using a sonic spraying technique, the resulting matrix becomes significantly stiffer than uncoated matrix. This characteristic is undesirable during clinical applications because of its inability to fully drape around uneven organ surfaces and, correspondingly, not lead to optimal sealing of the tissue surface. To address this problem, the coated matrix was pliabilized. Pliabilization was achieved by compressing using a metal roller. This imparts greater flexibility to the coated matrix material. Further, it is important to increase flexibility without removing coating materials while retaining coating density, friability and efficacy.

Example 5: Increase the Pliability of a Coated Stiffened Substrate Matrix

A method of increasing the pliability of a planar substrate matrix (e.g., ORC+fibers composed of a copolymer made from 90% glycolide and 10% L-lactide) spray coated with one or more PEG compositions (e.g., PEG-NH2+PEG-NHS) comprising the step of compressing the spray coated substrate matrix with a metal roller.

A carrier substrate matrix of made of an ORC+polyglactin 90:10 matrix was coated with PEG-NHS-10K (18 mg/cm$^2$) 4 arm and PEG-NH2-5K (7.5 mg/cm$^2$) 4 arm in the molar ratio of 1.2. This coated matrix was found to be efficacious in an animal model. However, the same coated matrix construction after coating with the PEG materials did not easily conform to irregular tissue surfaces. A sample of the coated matrix material was then compressed against a flat metal surface using a metal roller. This modified coated matrix material was then used and demonstrated significant improvement in conforming to irregular tissue surfaces.

Procedure:
1. Obtain four 2"×4" sections of coated matrix material—test samples.
2. Apply pressure by rolling a cylindrical stainless steel over or by direct compression on the coated side of test samples, rolling direction was along the sample's length. Rolling was different for each sample (conditions below: A, B, and D).
   A: Rolling a cylindrical stainless-steel weight with a mass of 885 grams rolled back and forth three times (three trips) along the length of the sample.
   B: Rolling a cylindrical stainless-steel weight with a mass of 5650 grams rolled back and forth one time (one trip) along the length of the sample.
   D: Directly apply the pressure over the surface of the sample for about 3 seconds with a weight having a mass of 5650 grams.

Condition A—control and compressed have minimal difference in degree of deflection, less than 5 degrees.
Condition B—control had maximum degree of difference about 30 degree of deflection
Condition D—control had modest degree of difference for deflection, 7 degrees.

Example 6

A carrier substrate matrix made of an ORC+polyglactin 90:10 matrix was coated with PEG-NHS-10K (18 mg/cm$^2$) 4 arm and PEG-NH2-5K (7.5 mg/cm$^2$) 4 arm in the molar ratio of 1.2. The impact of different contact surface designs (square knob, longitudinal knob, no knob as considered a flat surface) of rollers was explored with varying dead weights (900 grams, 5650 grams, 8190 grams). Samples information: Matrix as described above with 4-arm PEG-NH2-5K/PEG-NHIS-10K.

Procedure:
1. Obtain four 2"×4" sections of coated matrix material—test samples.
2. Weigh each 2"×4" sample, record as "Weight Before"
3. Apply pressure by rolling a cylindrical stainless steel covered with polymeric layer printed on its surface in combination with weight following the design in Table 1 over on the coated side of test samples, rolling direction was along the sample's length.
4. Re-weigh the sample and record as "Weight After"

Samples were tested for 3-point bending to quantify flexibility.

| Order number | Weight of system (g) | Weight level | Surface morphology |
|---|---|---|---|
| 1 | 5650 | Medium | Square knob |
| 2 | NA | Control | NA |
| 3 | 900 | Low | Longitudinal knob |
| 4 | 900 | Low | No knob |
| 5 | 8190 | High | No knob |
| 6 | 5650 | Medium | No knob |
| 7 | 8190 | High | Longitudinal knob |
| 8 | 8190 | High | Square knob |
| 9 | 900 | Low | Square knob |
| 10 | 5650 | Medium | Longitudinal knob |

TABLE 1

A (2$^3$) DOE design, Factors: Weight (3) and Surface Type (3) Friability was measured using the recorded weights before and after applying the weight roller.

| Order number | Weight of system (g) | Weight | Surface morphology | Weight before (mg) | Weight After (mg) | Friability (%) |
|---|---|---|---|---|---|---|
| 1 | 5650 | Medium | Square knob | 2246.8 | 2255.5 | 0% |
| 2 | NA | Control | | 2360.5 | 2389.0 | −1% |
| 3 | 900 | Low | Longitudinal knob | 2325.4 | 2339.1 | −1% |
| 4 | 900 | Low | No knob | 2262.3 | 2274.4 | −1% |
| 5 | 8190 | High | No knob | 2276.8 | 2297.6 | −1% |
| 6 | 5650 | Medium | No knob | 2359.9 | 2383.7 | −1% |
| 7 | 8190 | High | Longitudinal knob | 2316.8 | 2343.5 | −1% |
| 8 | 8190 | High | Square knob | 2350.8 | 2361.5 | 0% |
| 9 | 900 | Low | Square knob | 2353.3 | 2381.2 | −1% |
| 10 | 5650 | Medium | Longitudinal knob | 2290.4 | 2307.1 | −1% |

The results suggest that minimal friability was caused by this procedure hence most of reactive materials remain on the samples using this pliabilization method.

Example 7: Quantify Flexibility Using 3-Point Bending Test

Figure 5:
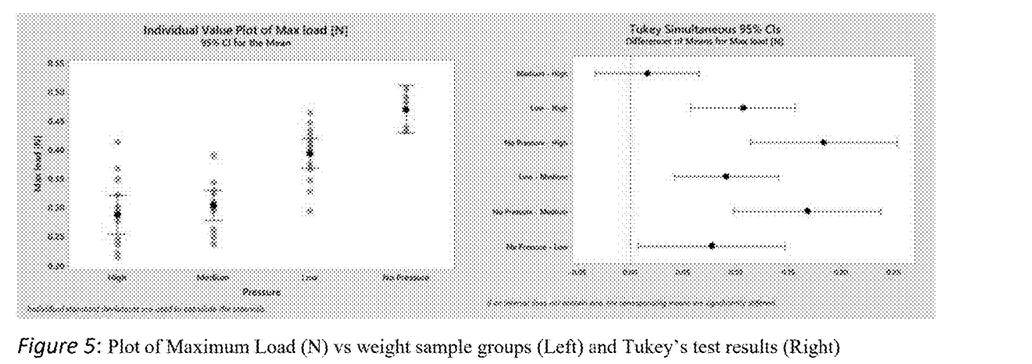
FIG. 5 illustrates a plot of maximum load versus weight.
Figure 6:
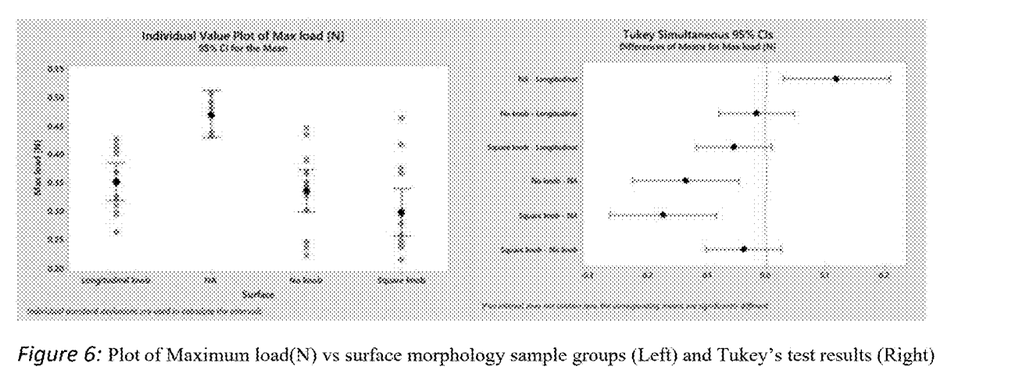
FIG. 6 illustrates a plot of maximum load versus surface morphology.

Pressure has an effect on flexibility: The results shown in FIG. 5 demonstrates that when using 900 grams weight rolling over the coated side of the sample 3 trips the flexibility significantly improved compared to control. When using 5650 grams metal rolling over the coated side of the sample 1 trip, the flexibility of the coated matrix significantly increases even higher than that of the 900 g. However, when using 8190 grams metal roller over the coated side of the samples, the resulted flexibility of the matrix was not significantly different from that of the 5650 grams which suggest that the flexibility have reached the plateau.

Surface morphology of the roller weighted surface has no significant effect on flexibility. It was found that a minimum of 900 grams used significantly improved pliability of sample than that of control and 5650 grams weight applied yielded significantly more pliable sample when compared to 900 grams. Applying higher weight (8190 grams) did not yield higher flexibility of test sample when compare to 5650 grams. Together, this results demonstrated that 900 grams to 5650 grams is the range in which these test materials could be effectively pliabilized for the tested materials. However, the results suggest that the surfaces morphology designs explored had no significant impact on the pliability of the test samples. Note that the contact surface of the roller is SLA for the different knob morphology while the no knob group, the contact surface was metal.

Example 8

A carrier matrix material (FIG. 1 (First Coating Order a)), such as a matrix fabricated from oxidized regenerated cellulose (ORC) and polyglactin 90:10, is coated with 4-arm-OK PEG-NH2*HCl and 4-arm-10K PEG-NS using an ultrasonic spraying technique. The samples were processed using the same procedure as described in Example 1 and the contact surfaces are all metal. Samples information: Amine Salt Matrix as described above with PEG-NH$_2$.HCL-10K+

PEG-NHIS-10K+ disodium tetraborate sprayed first and an Unbuffered Matrix/4arm PEG-NH$_2$/4arm PEG-SG-10K)

| Sample # | Samples Form (condition) | Dead weight (g) | Sample Weight Before (mg) | Sample Weight After (mg) | Friability (%) |
|---|---|---|---|---|---|
| A | Protected Amine salt-Rolling with 885 g for 3 trips | 885 | 2708.3 | 2712.3 | 0.15% |
| B | Protected Amine salt-Rolling with 5650 g for 1 trip | 5650 | 2873.8 | 2878.6 | 0.17% |
| C | Protected Amine salt-Control (no pressure applied) | NA | 2824.8 | 2830 | 0.18% |
| D | Protected Amine salt-Rolling with 2540 g for 1 trip | 2540 | 2807.8 | 2810.3 | 0.09% |
| E | Protected Amine salt-Directly compressed with 5650 g for 1 trip | 5650 | 2887.4 | 2887 | −0.01% |
| F | SOA Control (no pressure) | NA | 1165.7 | 1166.3 | 0.05% |
| G | SOA rolling with 5650 g for 6 round trips | 5650 | 1186.7 | 1188.8 | 0.18% |
| H | S1 rolling with 5650 g for 1 trip | 5650 | 2197.2 | 2199.2 | 0.09% |

Note:
1. All pressure was applied on reactive coated side (when present)
2. One trip means to roll over back and forth along the sample length (a round trip)

Procedure:
1. Weigh each sample and record the weight as "Before weight"
2. Take picture with control sample "Before picture"
3. Apply weight by rolling
4. Weigh sample and record the weight as "After weight"

The qualitative results from this example show that there is a minimum weight required to achieve flexibility results, a minimum of 5650 grams is needed for this Amine Salt (B) formulation, while only 900 gram weight was enough to pliabilize the non-amine formulation, by rolling back and forth 3 times, shown in Experiment 2.

The resulted increase flexibility of tested sample of both the amine salt and non-amine salt samples by rolling 5650-gram weight over the coated side back and forth once are similarly observed by the similar angle of deflection for both formulations (B and H)

The pliabilization of samples from both formulations were achieved with minimal loss of reactive powders. However, the SOA wound dressing could not be pliabilized using the same procedure. Upon further analysis on pliability of the tested samples using 3-point bending, the results are as follow.

| Sample Number | Samples Condition | AVG (N) | STDV |
|---|---|---|---|
| A | Protected Amine salt-Rolling with 885 g 3 trips | 0.4690 | 0.0452 |
| B | Protected Amine salt-Rolling with 5650 g 1 trip | 0.4033 | 0.0163 |
| C | Protected Amine salt-Control (no pressure applied) | 0.6006 | 0.0803 |
| D | Protected Amine salt-Rolling with 2540 g 1 trip | 0.4881 | 0.0626 |
| E | Protected Amine salt-Directly compressed with 5650 g once | 0.5505 | 0.0466 |
| F | Control-SOA | 1.1535 | 0.0714 |
| G | SOA Rolling with 5650 g 6 round trips | 1.0170 | 0.3049 |
| H | S1 Rolling with 5650 g 1 trip | 0.3432 | 0.0327 |

Grouping Information Using the Tukey Method and 95% Confidence

| Sample | N | Mean | Grouping | | | | |
|---|---|---|---|---|---|---|---|
| F | 4 | 1.1535 | a | | | | |
| G | 4 | 1.0170 | | b | | | |
| C | 5 | 0.6006 | | | c | | |
| E | 5 | 0.5505 | | | c | d | |
| D | 5 | 0.4881 | | | | d | e |
| A | 5 | 0.4690 | | | | d | e |
| B | 5 | 0.4033 | | | | | e | f |
| H | 5 | 0.3432 | | | | | | f |

Means that do not share a letter are significantly different. Based on the 3-point bending results it can be conclude as follows:
1. 885 grams weight by rolling back and forth on the coated side of the sample 3 times (Sample A), significantly increases pliability compared to control (Sample C). This result suggests that 885 grams over 3 trips is sufficient to pliabilize the samples.
2. 885 grams by rolling back and forth on the coated side of the sample 3 times (Sample A), does not increase the pliability compared to the sample with 5650 grams 1 trip (Sample B). This result suggests that 885 grams over 3 trips and 5650 grams over 1 trip can achieve similar pliability and this pliability achieved was significantly higher that than of the control (Sample C).
3. 2540 grams weight over the coated side of the sample 1 trip (Sample D), significantly increased the pliability compared to the control (Sample C)
4. Increasing the weight of the metal cylinder from 2540-gram weight (Sample D) to 5650 grams (sample B), significantly increases the pliability of the samples
5. Directly compressed samples with 5650 grams (sample E) were significantly less pliable than that of sample rolled over by 5650 grams weight over 1 trip (sample B)
6. Directly compressed with 5650 g weight (Sample E) was similar to that of the control (sample C)
7. Compressed SOA samples by roller of 5650 grams weight over 6 trips was similar to that of the SOA control
8. Sample B and Sample H pliabilized using the 5650 grams weight were comparable.

We claim:
1. A multi-layered wound dressing consisting of:
   a. a bi-layer carrier substrate consisting of a layer of oxidized cellulose joined to a layer of fibers composed of a copolymer made from 90% glycolide and 10% L-lactide;

b. a coating consisting of stacked spray-coated layers of
a layer of alkaline buffer immediately on the carrier substrate,
a layer of PEG-N-hydroxysuccinimide, and
a layer of protected PEG-amine end-capped with a plurality of hydrohalide protective leaving groups between the layer of alkaline buffer and the layer of PEG-N-hydroxysuccinimide,
wherein the alkaline buffer is disodium tetraborate, bis-tris methane (Bis-Tris), or 2-(N-morpholino) ethanesulfonic acid (MES).

2. The multilayered wound dressing according to claim 1, wherein the carrier substrate has at least two chemically distinct layers that are structurally integrated via ultrasonic welding, needle punching, heat welding, chemical attachment, suture attachment or combinations thereof.

3. The multi-layered wound dressing according to claim 1 wherein the hydrohalide protective leaving group reacts with the alkaline buffer to render a primary amine group available for reaction.

4. The multi-layered wound dressing of claim 1 that has been subjected to pliabilization to increase flexibility.

* * * * *